(12) United States Patent
Boehm et al.

(10) Patent No.: US 7,521,556 B2
(45) Date of Patent: *Apr. 21, 2009

(54) 1,6,9,14-TETRASUBSTITUTED TERRYLENE TETRACARBOXYLIC ACID DIIMIDES

(75) Inventors: Arno Boehm, Mannheim (DE); Matthias Krieger, Loerrach (DE); Erik Reuther, Mainz (DE); Klaus Muellen, Cologne (DE)

(73) Assignees: BASF SE, Ludwigshafen (DE); Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 405 days.

This patent is subject to a terminal disclaimer.

(21) Appl. No.: 10/514,568

(22) PCT Filed: Jun. 4, 2003

(86) PCT No.: PCT/EP03/05817

§ 371 (c)(1),
(2), (4) Date: Apr. 29, 2005

(87) PCT Pub. No.: WO03/104232

PCT Pub. Date: Dec. 18, 2003

(65) Prior Publication Data

US 2005/0222416 A1     Oct. 6, 2005

(30) Foreign Application Priority Data

Jun. 7, 2002     (DE) .................... 102 25 595

(51) Int. Cl.
*C07D 471/02* (2006.01)
*D06P 1/00* (2006.01)

(52) U.S. Cl. ............ 546/26; 8/636; 8/648; 252/301.26; 252/301.16

(58) Field of Classification Search ........... 546/26; 252/301.16, 301.26; 8/636, 648
See application file for complete search history.

(56) References Cited

U.S. PATENT DOCUMENTS 7,145,010 B2 * 12/2006 Boehm et al. ............... 546/26

FOREIGN PATENT DOCUMENTS

| AU | 2002-310976 | 10/2002 |
| WO | 02/076988 | 10/2002 |
| WO | WO 02/076988 | 10/2002 |

OTHER PUBLICATIONS

Holtrup, Frank O. et al. "Terrylenimides: New NIR Fluorescent Dyes", Chemistry- A European Journal, vol. 3, No. 2, pp. 219-225, XP000931226, ISSN: 0947-6539 1997.
Mais, S. et al. "Terrylenediimide: A Novel Fluorophore for Single-Molecule Spectroscopy and Microscopy from 1.4 K to Room Temperature", J. Phys. Chem. vol. 101, No. 45, pp. 8435-8440, 1997.

* cited by examiner

*Primary Examiner*—Charanjit S Aulakh
(74) *Attorney, Agent, or Firm*—Oblon, Spivak, McClelland, Maier & Neustadt, P.C.

(57) ABSTRACT

1,6,9,14-Tetrasubstituted terrylenetetracarboxylic diimides are particularly useful for absorbing and emitting in the long-wavelength red and near infrared region of the electromagnetic spectrum.

13 Claims, No Drawings

1,6,9,14-TETRASUBSTITUTED TERRYLENE TETRACARBOXYLIC ACID DIIMIDES

The present invention relates to novel 1,6,9,14-tetrasubstituted terrylenetetracarboxylic diimides of the general formula I

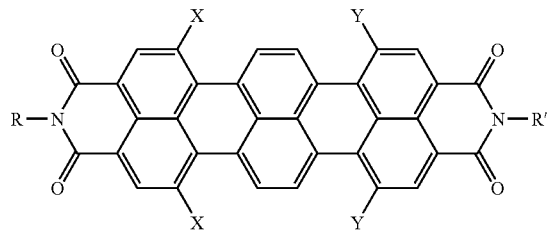

in which the variables are defined as follows:
X and Y are each independently
  bromine; cyano;
  aryloxy, arylthio, hetaryloxy or hetarylthio, each of which may be mono- or polysubstituted by $C_1$-$C_{12}$-alkyl, $C_1$-$C_{12}$-alkoxy, —$COOR^1$, —$SO_3R^1$, halogen, hydroxyl, carboxyl, cyano, —$CONHR^2$ and/or —NH$COR^2$;
  a radical of the formula -L-$R^3$;
  a radical of the formula —$NR^2_2$;
R and R' are each independently
  hydrogen;
  $C_1$-$C_{30}$-alkyl whose carbon chain may be interrupted by one or more —O—, —S—, —$NR^1$—, —CO— and/or —$SO_2$— groups, and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical which is bonded via a nitrogen atom and may contain further heteroatoms and be aromatic;
  $C_5$-$C_8$-cycloalkyl whose carbon skeleton may be interrupted by one or more —O—, —S— and/or —$NR^1$— groups, and/or which may be mono- or polysubstituted by $C_1$-$C_6$-alkyl;
  aryl or hetaryl which may be mono- or polysubstituted by $C_1$-$C_{18}$-alkyl, $C_1$-$C_6$-alkoxy, cyano, —$CONHR^2$, —$NHCOR^2$ and/or aryl or hetarylazo, each of which may be substituted by $C_1$-$C_{10}$-alkyl, $C_1$-$C_6$-alkoxy or cyano
1,2-ethylene, 1,2-ethenylene or 1,2-ethynylene;
$R^1$ is hydrogen or $C_1$-$C_6$-alkyl;
$R^2$ is hydrogen; $C_1$-$C_{18}$-alkyl; aryl or hetaryl, each of which may be substituted by $C_1$-$C_6$-alkyl, $C_1$-$C_6$-alkoxy, halogen, hydroxyl, carboxyl or cyano;
is $C_1$-$C_{18}$-alkyl whose carbon chain may be interrupted by one or more —O—, —S—, —$NR^1$—, —CO— and/or —$SO_2$— groups, and may be mono- or polysubstituted by —$COOR^1$, —$SO_3R^1$, hydroxyl, cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical which is bonded via a nitrogen atom and may contain further heteroatoms and be aromatic, and also to the preparation of these terrylenetetracarboxylic diimides and to their use for coloring high molecular weight organic and inorganic materials, as dispersing aids, pigment additives for organic pigments and intermediates for preparing fluorescent colorants and pigment additives, for preparing aqueous polymer dispersions which are colored or absorb and/or emit in the near infrared region of the electromagnetic spectrum, as photoconductors in electrophotography, as emitters in electroluminescence and chemiluminescence applications, as active components in fluorescence conversion, in bioluminescence arrays and also photovoltaics, and as laser dyes.

As J. Phys. Chem. A 1997, 101, p. 8435-8440 and Chem. Eur. J. 1997, 3, p. 219-225 disclose, terrylene-3,4:11,12-tetracarboxylic diimides (hereinafter referred to as "terrylimides" for short) are advantageously suitable as pigments and fluorescent colorants having absorption in the long-wavelength red and fluorescence emission in the long-wavelength red to near infrared region of the electromagnetic spectrum. Specifically, Chem. Eur. J. 1997, 3, p. 219-225 describes the preparation of core-unsubstituted and 1,6-di-tert-butylphenoxy-substituted terrylimides.

While the representatives of this substance class which are unsubstituted on the terrylene core are accessible in satisfactory yields via the synthetic sequence described, preparation of the 1,6-disubstituted derivatives is synthetically extremely complicated and delivers the products desired only in unsatisfactory yields. Preparation of more highly substituted derivatives having longer-wavelength absorption and emission is impossible in principle via the existing route.

It is an object of the present invention to provide more highly substituted terrylimides which have advantageous application properties and can in particular not only be incorporated efficiently into the particular application medium and be adapted to this medium, but also absorb and emit at longer wavelengths than the existing representatives of this substance class, i.e. in the long-wavelength red and near infrared region of the electromagnetic spectrum.

We have found that this object is achieved by the terrylimides of the formula I defined at the outset.

Preferred terrylimides can be taken from the subclaim.

A process has furthermore been found for preparing 1,6,9,14-tetrasubstituted terrylimides of the general formula Ia

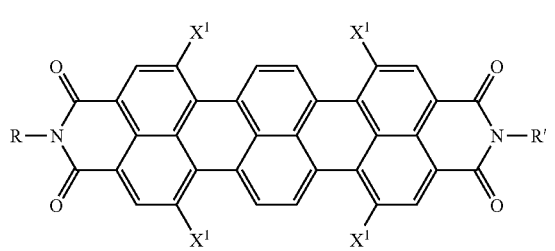

in which $X^1$ is bromine; aryloxy, arylthio, hetaryloxy or hetarylthio, each of which may be mono- or polysubstituted by $C_1$-$C_{12}$-alkyl, $C_1$-$C_{12}$-alkoxy, —$COOR^1$, —$SO_3R^1$, halogen, hydroxyl, carboxyl, cyano, —$CONHR^2$ and/or —NH$COR^2$, which comprises a) reacting a terrylimide of the general formula II

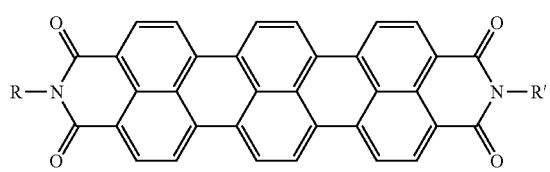

with elemental bromine in the presence of a halohydrocarbon as solvent to give the 1,6,9,14-tetrabromoterrylimide of the general formula Ia'

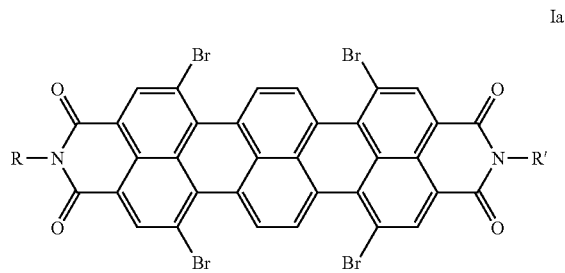

Ia' and if desired, b) converting the tetrabromoterrylimide Ia' obtained in step a) in the presence of an inert nitrogen-basic solvent and a base with an alcohol or thioalcohol of the general formula III where $X^1 \neq$ bromine $$X^1\text{—H} \qquad\qquad\qquad III$$

to the 1,6,9,14-tetrasubstituted terrylimide of the formula Ia where $X^1 \neq$ bromine.

A process has also been found for preparing 1,6,9,14-tetrasubstituted terrylimides of the general formula Ib

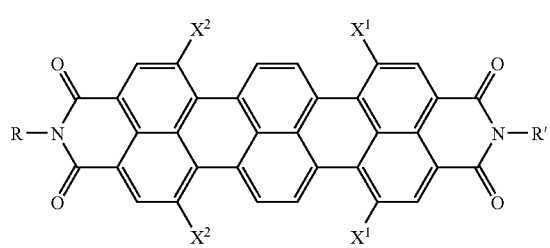

Ib in which $X^2$ is aryloxy, arylthio, hetaryloxy or hetarylthio, each of which may be mono- or polysubstituted by $C_1$-$C_{12}$-alkyl, $C_1$-$C_{12}$-alkoxy, —COOR$^1$, —SO$_3$R$^1$, cyano, —CONHR$^4$ and/or —NHCOR$^4$;

$y^2$ is bromine; aryloxy, arylthio, hetaryloxy or hetarylthio, each of which may be mono- or polysubstituted by $C_1$-$C_{12}$-alkyl, $C_1$-$C_{12}$-alkoxy, —COOR$^1$, —SO$_3$R$^1$, halogen, hydroxyl, carboxyl, cyano, —CONHR$^2$ and/or —NHCOR$^2$; and $R^4$ is $C_1$-$C_{18}$-alkyl; aryl or hetaryl, each of which may be substituted by $C_1$-$C_6$-alkyl, $C_1$-$C_6$-alkoxy, hydroxyl or cyano, which comprises a) reacting a 1,6-disubstituted terrylimide of the general formula IV

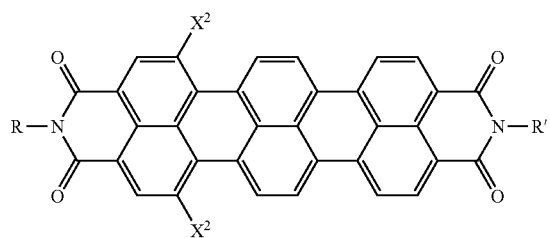

IV with elemental bromine in the presence of a halohydrocarbon as solvent to give the 9,14-dibrominated terrylimide of the general formula Ib'

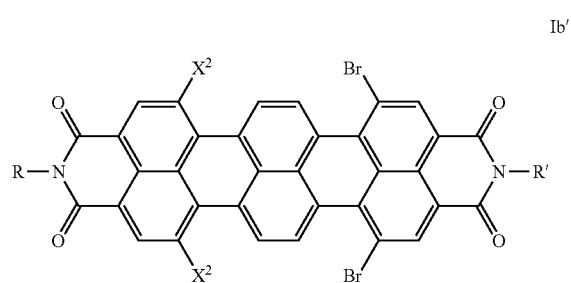

Ib' and, if desired, b) converting the 9,14-dibrominated terrylimide Ib' obtained in step a) in the presence of an inert nitrogen-basic solvent and a base with an alcohol or thioalcohol of the general formula III where $X^1 \neq$ bromine $$X^1\text{—H} \qquad\qquad\qquad III$$

to the 1,6,9,14-tetrasubstituted terrylimide of the formula Ib where $X^1 \neq$ bromine.

A process has also been found for preparing 1,6,9,14-tetrasubstituted terrylimides of the general formula Ic

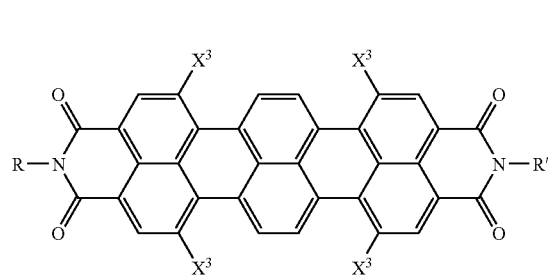

Ic in which $X^3$ is a radical of the formula -L-R$^3$, which comprises reacting a 1,6,9,14-tetrabromoterrylimide of the general formula dadurch Ia'

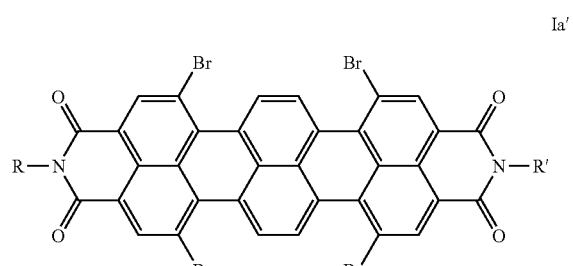

Ia' in the presence of an aprotic solvent, a palladium complex as a catalyst, a copper salt as a cocatalyst and a base with a 1-alkyne of the general formula V $$H\text{—}C\equiv C\text{—}R^3 \qquad\qquad\qquad V$$

and, if desired, additionally reducing the unsaturated bonds present in the $X^3$ radicals of the 1,6,9,14-tetrasubstituted terrylimide obtained.

Finally, a process has been found for preparing 1,6,9,14-tetrasubstituted terrylimides of the general formula Id

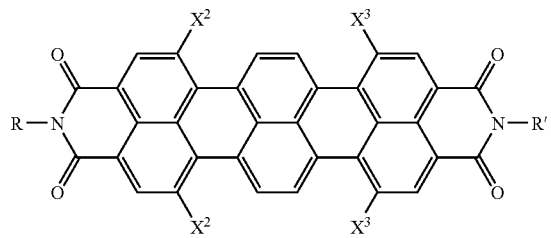

in which
X² is aryloxy, arylthio, hetaryloxy or hetarylthio, each of which may be mono- or polysubstituted by $C_1$-$C_{12}$-alkyl, $C_1$-$C_{12}$-alkoxy, —$COOR^1$, —$SO_3R^1$, cyano, —$CONHR^4$ and/or —$NHCOR^4$;
X³ is a radical of the formula -L-R³ and
R⁴ is $C_1$-$C_{18}$-alkyl; aryl or hetaryl, each of which may be substituted by $C_1$-$C_6$-alkyl, $C_1$-$C_6$-alkoxy, hydroxyl or cyano,
which comprises reacting a 9,14-dibrominated terrylimide of the general formula Ib' in the presence of an aprotic solvent, a palladium complex as a catalyst, a copper salt as a cocatalyst and a base with a 1-alkyne of the general formula V

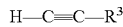 V and, if desired, additionally reducing the unsaturated bonds present in the X³ radicals of the 1,6,9,14-tetrasubstituted terrylimide obtained.

Last but not least, the use has been found of the terrylimides I for coloring high molecular weight organic and inorganic materials, as dispersing aids, pigment additives for organic pigments and intermediates for preparing fluorescent colorants and pigment additives, for preparing aqueous polymer dispersions which are colored or absorb and/or emit in the near infrared region of the electromagnetic spectrum, as photoconductors in electrophotography, as emitters in electroluminescence and chemiluminescence applications, as active components in fluorescence conversion, in bioluminescence arrays and also photovoltaics, and as laser dyes.

All alkyl groups occurring in the formulae I to V may be straight-chain or branched. When the alkyl groups are substituted, they generally bear 1 or 2 substituents.

Aromatic radicals which are substituted may generally have up to 3, preferably 1 or 2, of the specified substituents.

Preferred -L-R³ radicals are ethenyl and ethynyl, each of which is substituted by $C_1$-$C_{18}$-alkyl, in particular $C_4$-$C_8$-alkyl, which may in particular be terminally (ω-position) substituted by cyano, hydroxyl, carboxyl, methylcarboxyl or ethylcarboxyl.

Specific examples of suitable R, R', $R^1$, $R^2$, $R^3$, $R^4$, X, $X^1$, $X^2$, $X^3$, Y and $Y^2$ radicals (and of their substituents) and also -L-R³ are as follows:
methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process);
methoxymethyl, 2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl;
methylthiomethyl, 2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;
2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;
propan-2-on-1-yl, butan-3-on-1-yl, butan-3-on-2-yl and 2-ethylpentan-3-on-1-yl;
2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;
carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;
sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;
2-hydroxyethyl, 3-hydroxypropyl, 1-hydroxyprop-2-yl, 2- and 4-hydroxybutyl, 1-hydroxybut-2-yl and 8-hydroxy-4-oxaoctyl;
cyanomethyl, 2-cyanoethyl, 3-cyanopropyl, 2-methyl-3-ethyl-3-cyanopropyl, 7-cyano-7-ethylheptyl and 4,7-dimethyl-7-cyanoheptyl;
methoxy, ethoxy, propoxy, isopropoxy, butoxy, isobutoxy, sec-butoxy, tert-butoxy, pentoxy, isopentoxy, neopentoxy, tert-pentoxy and hexoxy;
carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;
formylamino, acetylamino, propionylamino and benzoylamino; chlorine, bromine and iodine;
phenylazo, 2-napthylazo, 2-pyridylazo and 2-pyrimidylazo;
phenyl, 1- and 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

2-, 3- and 4-methylphenyl, 2,3-, 2,4-, 2,5-, 3,5- and 2,6-dimethylphenyl, 2,4,6-trimethylphenyl, 2-, 3- and 4-ethylphenyl, 2,3-, 2,4-, 2,5-, 3,5- and 2,6-diethylphenyl, 2,4,6-triethylphenyl, 2-, 3- and 4-propylphenyl, 2,3-, 2,4-, 2,5-, 3,5- and 2,6-dipropylphenyl, 2,4,6-tripropylphenyl, 2-, 3- and 4-isopropylphenyl, 2,3-, 2,4-, 2,5-, 3,5- and 2,6-diisopropylphenyl, 2,4,6-triisopropylphenyl, 2-, 3- and 4-butylphenyl, 2,3-, 2,4-, 2,5-, 3,5- and 2,6-dibutylphenyl, 2,4,6-tributylphenyl, 2-, 3- and 4-isobutylphenyl, 2,3-, 2,4-, 2,5-, 3,5- and 2,6-diisobutylphenyl, 2,4,6-triisobutylphenyl, 2-, 3- and 4-sec-butylphenyl, 2,3-, 2,4-, 2,5-, 3,5- and 2,6-di-sec-butylphenyl and 2,4,6-tri-sec-butylphenyl, 2-, 3- and 4-tert-butylphenyl, 2,3-, 2,4-, 2,5-, 3,5- and 2,6-di-tert-butylphenyl, 2,4,6-tri-tert-butylphenyl; 2-, 3- and 4-methoxyphenyl, 2,3-, 2,4-, 2,5-, 3,5- and 2,6-dimethoxyphenyl, 2,4,6-trimethoxyphenyl, 2-, 3- and 4-ethoxyphenyl, 2,3-, 2,4-, 2,5-, 3,5- and 2,6-diethoxyphenyl, 2,4,6-triethoxyphenyl, 2-, 3- and 4-propoxyphenyl, 2,3-, 2,4-, 2,5-, 3,5- and 2,6-dipropoxyphenyl, 2-3- and 4-isopropoxyphenyl, 2,3-, 2,4-, 2,5-, 3,5- and 2,6-diisopropoxyphenyl and 2-, 3- and 4-butoxyphenyl; 2-, 3- and 4-chlorophenyl, and 2,3-, 2,4-, 2,5-, 3,5- and 2,6-dichlorophenyl; 2-, 3-und 4-hydroxyphenyl and 2,3-, 2,4-, 2,5-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-N-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl, 3-, 4- and 5-propylcyclooctyl, 2-dioxanyl, 4-morpholinyl, 2- and 3-tetrahydrofuryl, 1-, 2- and 3-pyrrolidinyl and 1-, 2-, 3- and 4-piperidyl;

phenoxy, phenylthio, 1- and 2-naphthyloxy, 1- and 2-naphthylthio, 2-, 3- and 4-pyridyloxy, 2-, 3- and 4-pyridylthio, 2-, 4- and 5-pyrimidyloxy and 2-, 4- and 5-pyrimidylthio;

dimethylamino, diethylamino, dipropylamino, diisopropylamino, dibutylamino, diisobutylamino, di-tert-butylamino, dipentylamino, dihexylamino, diphenylamino, di-o-tolylamino, di-m-tolylamino, di-p-tolylamino, di(4-cyanophenyl)amino;

1-propynyl, 1-butynyl, 1-pentynyl, 3-methyl-1-butynyl, 1-hexynyl, 3- and 4-methyl-1-pentynyl, 3,3-dimethyl-1-butynyl, 1-heptynyl, 3-, 4- and 5-methyl-1-hexynyl, 3,3-, 3,4- and 4,4-dimethyl-1-pentynyl, 3-ethyl-1-pentynyl, 1-octynyl, 3-, 4-, 5- and 6-methyl-1-heptynyl, 3,3-, 3,4-, 3,5-, 4,4 and 4,5-dimethyl-1-hexynyl, 3-, 4- and 5-ethyl-1-hexynyl, 3-ethyl-3-methyl-1-pentynyl, 3-ethyl-4-methyl-1-pentynyl, 3,3,4- and 3,4,4-trimethyl-1-pentynyl, 1-nonynyl, 1-decynyl, 1-undecynyl and 1-dodecynyl;

4-cyano-1-butynyl, 5-cyano-1-pentynyl, 6-cyano-1-hexynyl, 7-cyano-1-heptynyl and 8-cyano-1-octynyl;

4-hydroxy-1-butynyl, 5-hydroxy-1-pentynyl, 6-hydroxy-1-hexynyl, 7-hydroxy-1-heptynyl, 8-hydroxy-1-octynyl, 9-hydroxy-1-nonynyl, 10-hydroxy-1-decynyl, 11-hydroxy-1-undecynyl and 12-hydroxy-1-dodecynyl;

4-carboxy-1-butynyl, 5-carboxy-1-pentynyl, 6-carboxy-1-hexynyl, 7-carboxy-1-heptynyl, 8-carboxy-1-octynyl, 4-methylcarboxy-1-butynyl, 5-methylcarboxy-1-pentynyl, 6-methylcarboxy-1-hexynyl, 7-methylcarboxy-1-heptynyl, 8-methylcarboxy-1-octynyl, 4-ethylcarboxy-1-butynyl, 5-ethylcarboxy-1-pentynyl, 6-ethylcarboxy--1-hexynyl, 7-ethylcarboxy-1-heptynyl and 8-ethylcarboxy-1-octynyl;

1-propenyl, 1-butenyl, 1-pentenyl, 3-methyl-1-butenyl, 1-hexenyl, 3- and 4-methyl-1-pentenyl, 3,3-dimethyl-1-butenyl, 1-heptenyl, 3-, 4- and 5-methyl-1-hexenyl, 3,3-, 3,4- and 4,4-dimethyl-1-pentenyl, 3-ethyl-1-pentenyl, 1-octenyl, 3-, 4-, 5- and 6-methyl-1-heptenyl, 3,3-, 3,4-, 3,5-, 4,4 and 4,5-dimethyl-1-hexenyl, 3-, 4- and 5-ethyl-1-hexenyl, 3-ethyl-3-methyl-1-pentenyl, 3-ethyl-4-methyl-1-pentenyl, 3,3,4- and 3,4,4-trimethyl-1-pentenyl, 1-nonenyl, 1-decenyl, 1-undecenyl and 1-dodecenyl;

4-cyano-1-butenyl, 5-cyano-1-pentenyl, 6-cyano-1-hexenyl, 7-cyano-1-heptenyl and 8-cyano-1-octenyl;

4-hydroxy-1-butenyl, 5-hydroxy-1-pentenyl, 6-hydroxy-1-hexenyl, 7-hydroxy-1-heptenyl, 8-hydroxy-1-octenyl, 9-hydroxy-1-nonenyl, 10-hydroxy-1-decenyl, 11-hydroxy-1-undecenyl and 12-hydroxy-1-dodecenyl;

4-carboxy-1-butenyl, 5-carboxy-1-pentenyl, 6-carboxy-1-hexenyl, 7-carboxy-1-heptenyl, 8-carboxy-1-octenyl, 4-methylcarboxy-1-butenyl, 5-methylcarboxy-1-pentenyl, 6-methylcarboxy-1-hexenyl, 7-methylcarboxy-1-heptenyl, 8-methylcarboxy-1-octenyl, 4-ethylcarboxy-1-butenyl, 5-ethylcarboxy-1-pentenyl, 6-ethylcarboxy-1-hexenyl, 7-ethylcarboxy-1-heptenyl and 8-ethylcarboxy-1-octenyl.

The terrylimides Ia, Ia', Ib and Ib' according to the invention, which are brominated or bear 4 identical (het)aryloxy or (het)arylthio radicals in the 1,6,9,14-position, or bear 2 identical (het)aryloxy or (het)arylthio radicals in the 1,6-position and in the 9,14-position or bear 2 identical (het)aryloxy or (het)arylthio radicals in the 1,6-position and are brominated in the 9,14-position, may advantageously be prepared by the two processes according to the invention starting from the core-unsubstituted terrylimides II and 1,6-disubstituted terrylimides IV respectively, both of which are disclosed by the literature.

The terrylimides II and IV are initially converted in step a) to the 1,6,9,14-tetrabrominated terrylimides of the formula Ia' and the 9,14-brominated terrylimides of the formula Ib' respectively by reacting with elemental bromine.

The terrylimides Ia and Ib which are substituted on the terrylene core by optionally further functionalized (het)aryloxy or (het)arylthio radicals may be prepared in a further step b) by reacting the brominated terrylimides Ia' and Ib' respectively with an aromatic or heteroaromatic alcohol or thioalcohol III with exchange of bromine.

Step a) of the preparative process according to the invention, the reaction of the terrylimides II and IV with elemental bromine, is carried out in the presence of a halohydrocarbon as solvent.

Useful solvents are either aliphatic or aromatic halogenated hydrocarbons, and preference is given to the chlorinated hydrocarbons. Specific examples include methylene chloride, chloroform, 1,1,2,2-tetrachloroethane, chlorobenzene, dichlorobenzene (all isomers) and trichlorobenzene (all isomers), among which preference is given to chloroform, 1,1,2,2-tetrachloroethane and chlorobenzene.

Customarily, from 15 to 150 g, preferably from 70 to 100 g, of solvent per gram of terrylimide II or IV to be brominated are used.

The molar ratio of bromine to terrylimide depends on the starting material used. In general, for each bromine atom to be introduced, from 1 to 2 mol, preferably from 1.1 to 1.5 mol, of bromine are used per mole of II or IV.

In general, the presence of a halogenation catalyst is unnecessary. However, if acceleration of the bromination reaction is desired (by a factor of about from 1.5 to 3), it is recommended to add elemental iodine, preferably in an amount of from 1 to 5 mol %, based on the terrylimide II or IV.

The reaction temperature depends on the stability of the substituents on the imide nitrogen toward the halogenation conditions and is generally from 40 to 100° C., in the case of inert alkyl and cycloalkyl substituents preferably from 60 to 100° C., and in the case of aryl and hetaryl substitutents, which are only of low stability toward the halogenation conditions, preferably from 50 to 70° C.

Depending on the reactivity of the terrylimide II or IV to be brominated and the presence or absence of iodine, the bromination is customarily complete within from 2 to 24 hours.

In terms of apparatus, the procedure in step a) is advantageously as follows:

Solvent and terrylimide II or IV are initially charged, any catalyst and then, within from 5 to 10 min, the desired amount of bromine are added, the mixture is heated with stirring to the desired reaction temperature and stirring is continued at the reaction temperature with the exclusion of light for from 2 to 24 hours. After removing excess bromine with a vigorous nitrogen stream, the solvent is removed under reduced pressure. The residue is slurried in about 20 times the volume of an aliphatic alcohol, such as methanol, and stirred overnight. The product which has precipitated out is then filtered off, washed, preferably with the same alcohol and then with water, and dried at about 120° C. under reduced pressure.

In general, the purity of the 1,6,9,14-tetrabrominated terrylimides of the formula Ia' or the 9,14-dibrominated terrylimides of the formula Ib' prepared in this way are sufficient for further processing. If desired, purification may be carried out by column filtration on silica gel using methylene chloride as the eluent or by extraction with a solvent such as methanol.

Terrylimides Ia and Ib which are substituted on the terrylene core by optionally further functionalized (het)aryloxy or (het)arylthio radicals may be prepared in accordance with step b) of the process according to the invention by reacting the brominated terrylimides Ia' and Ib' respectively with an aromatic or heteroaromatic alcohol or thioalcohol III in the presence of an inert nitrogen-basic solvent and a base.

Particularly useful inert nitrogen-basic solvents for this purpose are polar solvents, in particular nitrogen heterocycles such as pyridine, pyrimidine, quinoline, isoquinoline, quinaldine and N-methylpyrrolidone, and also carboxamides such as N,N-dimethylformamide and N,N-dimethylacetamide, although preference is given to N-methylpyrrolidone.

Depending on the solubility of the brominated terrylimide Ia' or Ib', the amount of solvent is customarily from 5 to 100 g, preferably from 10 to 40 g, per gram of the terrylimide Ia' or Ib'.

Useful bases are in particular non-nucleophilic or only weakly nucleophilic compounds. Examples of such bases include inorganic bases, for example alkali metal hydroxides such as potassium hydroxide and sodium hydroxide, and alkali metal carbonates such as potassium carbonate and sodium carbonate, and also organic bases, for example alkali metal alkoxides, in particular tertiary alcohols, such as lithium tert-butoxide, sodium tert-butoxide and potassium tert-butoxide, which are used in anhydrous form.

In general, from 0.8 to 1.5, preferably from 1 to 1.3, molar equivalents of base are used per mole of bromine atom to be substituted.

The molar ratio of brominated terrylimide Ia' or Ib' to alcohol or thioalcohol III likewise depends on the number of bromine atoms to be substituted. In general, from 1 to 2 mol, preferably from 1 to 1.5 mol, of III are used per mole of bromine atom to be exchanged.

The reaction temperature is customarily in the range from 50 to 200° C., preferably from 60 to 140° C.

It is recommended to carry out the reaction under protective gas.

Depending on the reactivity of the brominated terrylimide Ia' or Ib', the reaction time is from about 2 to 48 h.

In terms of apparatus, the procedure in step b) is advantageously to initially charge the solvent, add brominated terrylimide Ia' or Ib', alcohol or thioalcohol III and base, and heat the resulting solution or suspension to the desired reaction temperature with stirring under protective gas for from 2 to 48 hours.

The reaction product may be isolated after cooling to room temperature by directly filtering off the reaction product which has already precipitated or by filtering off after diluting with from three to four times the volume of water, a dilute inorganic acid, for example from 5 to 10% by weight hydrochloric acid, or an aliphatic alcohol, for example methanol, washing, initially with a little solvent and then with water until the filtrate is neutral, and then drying under reduced pressure.

The terrylimides Ic according to the invention which bear 4 identical, if desired substituted, alkyl., alkenyl or alkynyl radicals $X^3$ in the 1,6,9,14-position may advantageously be prepared by the process according to the invention starting from the 1,6,9,14-tetrabromoterrylimides of the formula Ia' which are likewise according to the invention.

In this process, the tetrabromoterrylimides Ia' are reacted with an alkyne V. The unsaturated bond present in the $X^3$ substituent may, if desired, be additionally reduced.

The reaction with the alkyne V is carried out in the presence of an aprotic solvent, a palladium complex as catalyst, a copper salt as cocatalyst and a base.

Useful solvents in this case are linear and cyclic aliphatic ethers having up to 10 carbon atoms such as diethyl ether, di-n-propyl ether, di-n-butyl ether, 1,2-dimethoxyethane, 1,2-diethoxyethane, dioxane and in particular tetrahydrofuran.

Customarily, from 30 to 150 g, preferably from 50 to 80 g, of solvent are used per gram of tetrabromoterrylimide Ia'.

The base added serves at the same time as cosolvent. Useful bases for this purpose are in particular the organic nitrogen bases which are miscible with the ethers and have a melting point below room temperature and a boiling point above the reaction temperature.

Preferred bases are aliphatic amines having up to 15 carbon atoms, in particular tertiary amines, such as triethylamine, tri-n-propylamine and tri-n-butylamine, and cycloaliphatic amines, in particular piperidine.

Customarily, from 0.2 to 1.5 g, preferably from 0.7 to 1.2 g, of base are added per gram of solvent.

The catalysts used are palladium complexes which are used in combination with copper(I) salts as cocatalyst.

Examples of suitable palladium complexes include tetrakis (tris-o-tolylphosphine)palladium(0), [1,2-bis(diphenylphosphino)ethane]palladium(II) chloride, [1,1'-bis(diphenylphosphino)ferrocene]palladium(II) chloride, bis(triethylphosphine)palladium(II) chloride, bis(tricyclohexylphosphine)palladium(II) chloride, bis(triphenylphosphine)palladium(II) acetate, (2,2'-bipyridyl)palladium(II) chloride and in particular tetrakis(triphenylphosphine)palladium(0), bis(triphenylphosphine)palladium(II) chloride, bis(acetonitrile)palladium(II) chloride and bis(benzonitrile)palladium(II) chloride Examples of particularly suitable copper(I) salts include copper(I) iodide and copper(I) bromide.

In general, from 4 to 30 mol %, preferably from 10 to 20 mol %, of palladium complex, and generally from 4 to 40 mol %, preferably from 15 to 25 mol %, of copper(I) salt, based in each case on the tetrabromoterrylimide Ia', are used.

The molar ratio of tetrabromoterrylimide Ia' to alkyne V is generally from 1:4 to 1:8, in particular from 1:4 to 1:6.

The reaction temperature is customarily from 20 to 140° C., in particular from 40 to 90° C.

Depending on the alkyne V used, the reaction may be carried out at atmospheric pressure or at an elevated pressure of generally up to 50 bar. When using volatile alkynes such as acetylene, it is necessary to work under pressure.

The reaction generally takes from about 1 to 15 h, in particular from 2 to 10 h.

Depending on the reaction conditions selected, it is possible to prepare terrylimides Ic which contain 1,2-ethynylene or 1,2-ethenylene radicals as the bridging group L in the $X^3$ substituents.

To prepare terrylimides Ic having $X^3$ substituents containing unsaturated bonds, it is recommended to work under protective gas (for example argon or nitrogen). When the reaction time is over 4 h and/or the reaction temperature is over 100° C., the acetylenic bond is directly reduced to the ethylenic bond.

Terrylimides Ic containing ethylene radicals L may be obtained by continuing to stir the reaction mixture in a hydrogen atmosphere. However, a subsequent reduction of the unsaturated bond, for example with hydrogen under palladium/activated carbon catalysis, may be carried out using a procedure customary for such reductions (cf. Larock, Comprehensive Organic Transformations, VCH Publishers New York, 1989, p. 6-17; March, Advanced Organic Chemistry, John Wiley and Sons New York, 4th Edition 1992, p. 775-777; J. Org. Chem. 45, p. 4926-4931 (1980)).

The terrylimides Id according to the invention which are substituted in the 1,6-position by 2 identical, optionally further functionalized, (het)aryloxy or (het)arylthio radicals and bear 2 identical, if desired substituted, alkyl, alkenyl or alkynyl radicals $X^3$ in the 9,14-position, may advantageously be prepared by the process which is likewise according to the invention and starts from the 9,14-dibrominated terrylimide Ib', in a similar manner to the preparation of the terrylimides Ic using half of the amounts of palladium complex, copper(I) salt and alkyne V.

In terms of apparatus, the procedure in the process for preparing terrylimides Ic and Id is advantageously as follows:

A stirred solution or suspension of the tetrabromoterrylimide Ia or of the dibromoterrylimide Ib' is initially charged in a mixture of solvent and base (both substantially anhydrous), the suspension is saturated with nitrogen by repeated degassing and charging with dry nitrogen, and the copper(I) salt, the palladium complex and the alkyne V are introduced in the nitrogen countercurrent (volatile alkynes such as acetylene are injected preweighed into the closed apparatus) and the reaction mixture is heated to the desired reaction temperature for the desired time. If desired, hydrogen is then injected and stirring is continued at the reaction temperature for a further 4 to 8 hours. Afterwards (optionally after preceding decompression), the reaction mixture is introduced directly, i.e. without preceding cooling, with vigorous stirring into about three times the volumne of a mixture of about equal parts by weight of concentrated hydrochloric acid and ice, the crude product is filtered off, washed with semiconcentrated hydrochloric acid until the filtrate is colorless and then with water until the filtrate is neutral, and dried under reduced pressure.

The terrylimides of the general formula I according to the invention where X and/or Y=cyano or $-NR^2{}_2$ may be prepared by methods known from the literature and described, for example, in EP-A-264 543, WO-A-01/16109 and the preceding German patent application 101 08 601.6.

In general, the terrylimides I according to the invention already have such a high purity (>95%) that no further purification is necessary. Analytically pure products may be prepared by recrystallizing from aromatic solvents such as toluene and xylene, or halogenated hydrocarbons such as methylene chloride and chloroform, or by filtration of a solution of the products in these solvents through silica gel and subsequent concentration.

The terrylimides I according to the invention are outstandingly suitable for homogeneously coloring high molecular weight organic and inorganic materials, in particular, for example, plastics, in particular thermoplastics, coatings and printing inks, and also oxidic layer systems.

They are also suitable as dispersing aids, pigment additives for organic pigments and intermediates for preparing fluorescent colorants and pigment additives, for preparing aqueous polymer dispersions which are colored or absorb and/or emit in the near infrared region of the electromagnetic spectrum, as photoconductors in electrophotography, as emitters in electroluminescence and chemiluminescence applications, as active components in fluorescence conversion, in bioluminescence arrays and also photovoltaics, and as laser dyes.

The terrylimides I according to the invention customarily absorb at from 670 to 700 nm and generally emit at from 710 to 780 nm, and so their absorption and emmission occur at distinctly longer wavelengths than those of the known terrylimides.

EXAMPLES a) Preparation of the 1,6,9,14-tetrabrominated Terrylimides of the Formula Ia'

Examples 1 to 10

A mixture of x g (25 mmol) of terrylimide II, y g of iodine as catalyst, 20 g (125 mmol) of bromine and v ml of the solvent L were heated to T° C. with stirring and the exclusion of light for t h.

After cooling the reaction solution to room temperature and purging out excess bromine with nitrogen, the solvent was removed under reduced pressure. The crude product was slurried in 500 ml of methanol, stirred at room temperature for 12 h, filtered off, washed with methanol until the filtrate was almost colorless and then with water, dried and chromatographed on silica gel using dichloromethane as eluent. Further details on these experiments and also their results are compiled in table 1.

TABLE 1

| Ex. | Terrylimide II | x [g] | y [g] | Solvent L | v [ml] | t [h] | T [° C.] | Yield [g]/[%] | Apperance | m.p. [° C.] |
|---|---|---|---|---|---|---|---|---|---|---|
| 1 | N,N'-didodecylterrylimide | 21.3 | 0.13 | chlorobenzene | 2000 | 8 | 80 | 23.6/81 | blue-violet, microcrystaline | >300 |
| 2 | N,N'-di(5-nonyl)terrylimide | 19.2 | 0.13 | chlorobenzene | 1400 | 6 | 80 | 22.5/83 | blue-violet, microcrystalline | >300 |
| 3 | N,N'-dicyclohexylterrylimide | 17.0 | 0.13 | chlorobenzene | 1200 | 4 | 80 | 21.9/88 | blue, microcrystalline | >300 |
| 4 | N,N'-bis(2,6-diisopropylphenyl)terrylimide | 20.9 | 0.25 | chloroform | 1800 | 12 | 65 | 22.5/78 | blue, crystalline | >300 |
| 5 | N,N'-di(2-pyridyl)terrylimide | 16.7 | 0.25 | 1,1,2,2-tetra-chloroethane | 1650 | 16 | 65 | 18.0/73 | dark blue, crystalline | >300 |
| 6 | N-(2,6-diisopropylphenyl)-N'-methylterrylimide | 17.2 | 0.25 | 1,1,2,2-tetra-chloroethane | 1500 | 12 | 65 | 17.8/71 | dark blue, crystalline | >300 |
| 7 | N-(2,6-diisopropylphenyl)-N'-(5-nonyl)terrylimide | 20.0 | 0.25 | chloroform | 1500 | 12 | 65 | 20.9/75 | blue, microcrystalline | >300 |
| 8 | N-cyclohexyl-N'-(2,6-diisopropylphenyl)terrylimide | 18.9 | 0.25 | chloroform | 1400 | 12 | 65 | 19.8/74 | blue, microcrystalline | >300 |
| 9 | N-(2,6-diisopropylphenyl)-N'-(2-pyridyl)terrylimide | 18.8 | 0.25 | chloroform | 1800 | 12 | 65 | 20.5/77 | dark blue, crystalline | >300 |
| 10 | N-cyclohexyl-N'-methyl-terrylimide | 15.3 | 0.13 | chlorobenzene | 1500 | 6 | 80 | 18.5/80 | blue, microcrystalline | >300 |

Analytical Data on Example 4:

Elemental analysis (% by weight calc./found): C: 60.55/60.7; H: 3.7/3.7;; N: 2.45/2.45; O: 5.55/5.6; Br: 27.75/27.55; Mass (FD, 8 kV): m/z=1145.3 [M$^+$, 100%]; IR (KBr): $\nu$=1703 (s, C=O), 1660 (s, C=O) cm$^{-1}$; UV/VIS (CHCl$_3$): $\lambda_{max}$ ($\epsilon$)=559 (15850), 605 (46770), 656 (93330) nm.

Analytical Data on Example 8:

Elemental analysis (% by weight calc./found): C: 58.25/58.35; H: 3.4/3.4; N: 2.6/2.6; O: 5.95/6.0; Br: 29.8/29.65; Mass (FD, 8 kV): m/z=1073.0 [M$^+$, 100%]; IR (KBr): $\nu$=1705 (s, C=O), 1662 (s, C=O) cm$^{-1}$; UV/VIS (CHCl$_3$): $\lambda_{max}$ ($\epsilon$)=556 (16790), 600 (48290), 652 (90070) nm.

b) Preparation of the 9,14-dibrominated Terrylimides of the Formula Ib'

Examples 11 to 20

A mixture of x g (25 mmol) of terrylimide IV, y g of iodine as catalyst, 10 g (62.5 mmol) of bromine and v ml of solvent L were heated to T° C. with stirring and the exclusion of light for t h. After cooling the reaction solution to room temperature and purging out excess bromine with nitrogen, the solvent was removed under reduced pressure. The crude product was slurried in 500 ml of methanol, stirred at room temperature for 12 h, filtered off, washed with methanol until the filtrate was almost colorless and then with water, dried and chromatographed on silica gel using dichloromethane as eluent.

Further details on these experiments and also their results are compiled in table 2.

TABLE 2

| Ex. | Terrylimide IV | x [g] | y [g] | Solvent L | v [ml] | t [h] | T [° C.] | Yield [g]/[%] | Apperance | M.p. [° C.] |
|---|---|---|---|---|---|---|---|---|---|---|
| 11 | N,N'-didodecyl-1,6-diphenoxyterrylimide | 25.9 | 0.13 | 1,1,2,2-tetra-chloroethane | 2500 | 12 | 65 | 22.1/74 | dark blue, crystalline | >300 |
| 12 | N,N'-di(5'-nonyl)-1,6-di(p-tert-butylphenoxy) terrylimide | 26.6 | 0.13 | chloroform | 2100 | 12 | 60 | 25.9/85 | black-blue, amorphous | 295 |
| 13 | N,N'-dicyclohexyl-1,6-diphenoxyterrylimide | 21.6 | 0.13 | chloroform | 1600 | 12 | 60 | 20.7/81 | dark blue, amorphous | >300 |
| 14 | N,N'-bis(2',6'-diisopropylphenyl)-1,6-diphenoxyterrylimide | 25.5 | 0.13 | chloroform | 1800 | 12 | 60 | 22.7/77 | dark blue, microcrystalline | >300 |
| 15 | N,N'-bis(2',6'-diisopropylphenyl)-1,6-di(p-tert-butyl-phenoxy)terrylimide | 28.3 | 0.13 | chloroform | 2000 | 12 | 60 | 25.5/79 | dark blue, amorphous | 288 |
| 16 | N,N'-di(2'-pyridyl)-1,6-diphenoxyterrylimide | 21.3 | 0.13 | 1,1,2,2-tetra-chloroethane | 2100 | 12 | 65 | 14.0/72 | black-blue, crystalline | >300 |
| 17 | N-(2',6'-diisopropylphenyl)-N'-methyl-1,6-diphenoxyterrylimide | 21.8 | 0.13 | chloroform | 1750 | 12 | 65 | 19.8/77 | black-blue, microcrystalline | >300 |
| 18 | N-(2',6'-diisopropylphenyl)-N'-(5'-nonyl)-1,6-diphenoxyterrylimide | 24.6 | 0.13 | chloroform | 2000 | 12 | 60 | 21.7/76 | dark blue, microcrystalline | >300 |
| 19 | N-(2',6'-diisopropylphenyl)-N'-cyclohexyl-1,6-diphenoxyterrylimide | 23.5 | 0.13 | chloroform | 1750 | 12 | 60 | 22.5/82 | black-blue, crystalline | >300 |
| 20 | N-(2',6'-diisopropylphenyl)-N'-cyclohexyl-1,6-di(p-tert-butylphenoxy)terrylimide | 26.3 | 0.13 | chloroform | 1850 | 12 | 60 | 25.4/84 | dark blue, microcrystalline | 256 |

Analytical Data on Example 14:

Elemental analysis (% by weight calc./found): C: 71.45/71.6; H: 4.45/4.5; N: 2.4/2.4; O: 8.15/8.2; Br: 13.55/13.3; Mass (FD, 8 kV): m/z=1175.7 [M$^+$, 100%]; IR (KBr): $\nu$=1705 (s, C=O), 1,662 (s, C=O) cm$^{-1}$; UV/VIS (CHCl$_3$): $\lambda_{max}$ ($\epsilon$)=553 (9750), 616 (51330); 661 (111530) nm.

Analytical Data on Example 15:

Elemental analysis (% by weight calc./found): C: 72.65/72.7; H: 5.3/5.3; N: 2.2/2.2; O: 7.45/7.5; Br: 12.4/12.3; Mass (FD, 8 kV): m/z=1287.8 [M$^+$, 100%]; IR (KBr): $\nu$=1704 (s, C=O), 1662 (s, C=O) cm$^{-1}$; UV/VIS (CHCl$_3$): $\lambda_{max}$ ($\epsilon$)=551 (10080), 615 (55000), 659 (106780) nm.

Analytical Data on Example 19:

Elemental analysis (% by weight calc./found): C: 69.95/70.0; H: 4.2/4.2; N: 2.55/2.6; O: 8.75/8.8; Br: 14.55/14.4; Mass (FD, 8 kV): m/z=1198.0 [M$^+$, 100%]; IR (KBr): $\nu$=1705 (s, C=O), 1660 (s, C=O) cm$^{-1}$; UV/VIS (CHCl$_3$): $\lambda_{max}$ ($\epsilon$)=552 (11040), 616 (53790), 660 (113460) nm.

Analytical Data on Example 20:

Elemental analysis (% by weight calc./found):
C: 71.4/71.6; H: 5.15/5.2; N: 2.3/2.3; O: 7.95/8.0; Br: 13.2/12.9; Mass (FD, 8 kV): m/z=1209.9 [M$^+$, 100%]; IR (KBr): $\nu$=1705 (s, C=O), 1662 (s, C=O) cm$^{-1}$; UV/VIS (CHCl$_3$): $\lambda_{max}$ ($\epsilon$)=550 (10730), 614 (58490), 657 (111110) nm.

c) Preparation of the 1,6,9,14-tetrasubstituted Terrylimides of the Formula I where X and Y≠Br Examples 21 to 50

A mixture of x g (10 mmol) of the tetra- or dibrominated terrylimides Ia' or Ib' from example B, y g (y$_1$ mmol) of alcohol or thioalcohol III, z g (z$_1$ mmol) of anhydrous potassium carbonate and v ml of N-methylpyrrolidone were heated to T° C. with stirring under a protective gas atmosphere for t h. After cooling to room temperature, the reaction product was filtered off, either directly (examples 22, 30 and 32) or after diluting with 3 times the volume of 5% strength hydrochloric acid (examples 24, 26, 28, 29, 35, 36, 43, 45, 48, 49) or methanol (examples 21, 23, 25, 27, 31, 33, 34, 37-42, 44, 46, 47, 50), and then washed initially with a little solvent (examples 22, 30, 32) or the same mixture of solvent and diluent (examples 21, 23-29, 31, 33-50) and then with water until the filtrate is neutral and then dried at 120° C. under reduced pressure.

Further details on these experiments and also their results are compiled in Table 3.

TABLE 3

| Ex. | x [g] | Terrylimide from ex. | y [g] | y$_1$ [mmol] | (Thio)alcohol III | z [g] | z$_1$ [mmol] | v [ml] | t [h] | T [° C.] | Yield [g]/[%] | Appearance | m.p. [° C.] |
|---|---|---|---|---|---|---|---|---|---|---|---|---|---|
| 21 | 11.7 | 1 | 10.3 | 50 | tert-octyl-phenol | 3.45 | 25 | 300 | 8 | 80 | 13.8/83 | dark blue, microcrystalline | >300 |
| 22 | 11.7 | 1 | 6.6 | 60 | thiophenol | 4.15 | 30 | 300 | 12 | 70 | 10.0/78 | black-blue, microcrystalline | >300 |
| 23 | 10.8 | 2 | 4.25 | 45 | phenol | 3.10 | 22.5 | 250 | 6 | 95 | 9.3/82 | dark blue, amorphous | >300 |
| 24 | 9.95 | 3 | 7.5 | 50 | tert-butyl-phenol | 3.45 | 25 | 150 | 6 | 95 | 10.8/85 | dark blue, amorphous | >300 |
| 25 | 9.95 | 3 | 6.6 | 60 | thiophenol | 4.15 | 30 | 150 | 12 | 70 | 8.8/79 | black-blue, amorphous | >300 |
| 26 | 9.95 | 3 | 11.0 | 50 | p-iodo-phenol | 3.45 | 25 | 150 | 8 | 80 | 12.6/81 | dark blue, amorphous | >300 |
| 27 | 11.5 | 4 | 4.7 | 50 | phenol | 3.45 | 25 | 250 | 6 | 95 | 10.5/87 | dark blue, crystalline | >300 |
| 28 | 11.5 | 4 | 9.9 | 45 | p-iodo-phenol | 3.10 | 22.5 | 250 | 8 | 80 | 13.6/80 | dark blue, crystalline | >300 |
| 29 | 11.5 | 4 | 10.3 | 50 | tert-octyl-phenol | 3.45 | 25 | 250 | 8 | 80 | 13.2/80 | dark blue, crystalline | >300 |
| 30 | 11.5 | 4 | 6.6 | 60 | thiophenol | 4.15 | 30 | 250 | 12 | 70 | 9.8/77 | black-blue, microcrystalline | >300 |
| 31 | 9.85 | 5 | 10.3 | 50 | tert-octyl-phenol | 3.45 | 25 | 350 | 8 | 80 | 12.3/83 | dark blue, crystalline | >300 |
| 32 | 9.85 | 5 | 6.6 | 60 | thiophenol | 4.15 | 30 | 350 | 12 | 70 | 8.6/78 | black-blue, microcrystalline | >300 |
| 33 | 10.0 | 6 | 7.5 | 50 | tert-butyl-phenol | 3.45 | 25 | 300 | 6 | 95 | 10.8/84 | dark blue, crystalline | >300 |
| 34 | 11.2 | 7 | 7.5 | 50 | tert-butyl-phenol | 3.45 | 25 | 200 | 6 | 95 | 11.4/82 | dark blue, crystalline | >300 |
| 35 | 10.7 | 8 | 9.9 | 45 | p-iodo-phenol | 3.10 | 22.5 | 250 | 8 | 80 | 13.0/80 | dark blue, microcrystalline | >300 |
| 36 | 10.7 | 8 | 10.3 | 50 | tert-octyl-phenol | 3.45 | 25 | 250 | 8 | 80 | 12.9/82 | dark blue, crystalline | >300 |
| 37 | 10.7 | 8 | 6.6 | 60 | thiophenol | 4.15 | 30 | 250 | 12 | 70 | 9.0/76 | black-blue, microcrystalline | >300 |
| 38 | 10.7 | 9 | 10.3 | 50 | tert-octyl-phenol | 3.45 | 25 | 300 | 8 | 80 | 12.7/81 | dark blue, microcrystalline | >300 |
| 39 | 10.7 | 9 | 6.6 | 60 | thiophenol | 4.15 | 30 | 300 | 12 | 70 | 8.9/75 | black-blue, microcrystalline | >300 |
| 40 | 9.3 | 10 | 7.5 | 50 | tert-butyl-phenol | 3.45 | 25 | 350 | 6 | 95 | 9.6/80 | dark blue, microcrystalline | >300 |
| 41 | 11.95 | 11 | 3.3 | 30 | thiophenol | 2.10 | 15 | 200 | 12 | 70 | 9.6/77 | black-blue, microcrystalline | >300 |

TABLE 3-continued

| Ex. | x [g] | Terrylimide from ex. | y [g] | $y_1$ [mmol] | (Thio)alcohol III | z [g] | $z_1$ [mmol] | v [ml] | t [h] | T [°C.] | Yield [g]/[%] | Appearance | m.p. [°C.] |
|---|---|---|---|---|---|---|---|---|---|---|---|---|---|
| 42 | 12.2 | 12 | 3.3 | 30 | thiophenol | 2.10 | 15 | 150 | 12 | 70 | 9.6/75 | black-blue, amorphous | >300 |
| 43 | 8.65 | 13 | 5.5 | 25 | p-iodo-phenol | 1.75 | 12.5 | 100 | 8 | 80 | 10.5/81 | dark blue, amorphous | >300 |
| 44 | 10.2 | 14 | 3.3 | 30 | thiophenol | 2.10 | 15 | 200 | 12 | 70 | 9.8/79 | dark blue, microcrystalline | >300 |
| 45 | 11.3 | 15 | 5.5 | 25 | p-iodo-phenol | 1.75 | 12.5 | 150 | 8 | 80 | 13.0/83 | dark blue, amorphous | >300 |
| 46 | 8.55 | 16 | 3.3 | 30 | thiophenol | 2.10 | 15 | 200 | 12 | 70 | 8.1/76 | dark blue, microcrystalline | >300 |
| 47 | 10.3 | 17 | 3.3 | 30 | thiophenol | 2.10 | 15 | 200 | 12 | 70 | 8.6/79 | black-blue, microcrystalline | >300 |
| 48 | 11.45 | 18 | 5.5 | 25 | p-iodo-phenol | 1.75 | 12.5 | 200 | 8 | 80 | 11.7/82 | dark blue, amorphous | >300 |
| 49 | 9.4 | 19 | 5.5 | 25 | p-iodo-phenol | 1.75 | 12.5 | 150 | 8 | 80 | 11.7/85 | dark blue, amorphous | >300 |
| 50 | 10.55 | 20 | 3.3 | 30 | thiophenol | 2.10 | 15 | 150 | 12 | 70 | 10.2/80 | black-blue, amorphous | >300 |

Analytical Data on Example 27:
Elemental analysis (% by weight calc./found): C: 81.85/81.8; H: 5.2/5.2; N: 2.3/2.35; O: 10.65/10.65; Mass (FD, 8 kV): m/z=1202.7 [M$^+$, 100%]; IR (KBr): ν=1709 (s, C=O), 1668 (s, C=O) cm$^{-1}$; UV/VIS (CHCl$_3$): λ$_{max}$ (ε)=630 (61010), 678 (143210) nm.

Analytical Data on Example 28:
Elemental analysis (% by weight calc./found): C: 57.7/57.6; H: 3.4/3.4; N: 1.65/1.65; O: 7.5/7.55; I: 29.75/29.8; Mass (FD, 8 kV): m/z=1706.5 [M$^+$, 100%]; IR (KBr): ν=1708 (s, C=O), 1669 (s, C=O) cm$^{-1}$; UV/VIS (CHCl$_3$): λ$_{max}$ (ε)=626 (50330), 675 (124000) nm.

Analytical Data on Example 29:
Elemental analysis (% by weight calc./found): C: 82.85/82.8; H: 7.7/7.7; N: 1.7/1.7; O: 7.75/7.8; Mass (FD, 8 kV): m/z=1651.2 [M$^+$, 100%]; IR (KBr): ν=1708 (s, C=O), 1668 (s, C=O) cm$^{-1}$; UV/VIS (CHCl$_3$): λ$_{max}$ (ε)=625 (52930), 677 (128770) nm.

Analytical Data on Example 30:
Elemental analysis (% by weight calc./found): C: 77.7/77.5; H: 4.95/5.0; N: 2.2/2.2; O: 5.05/5.1; S: 10.1/10.2; Mass (FD, 8 kV): m/z=1266.9 [M$^+$, 100%]; IR (KBr): ν=1706 (s, C=O), 1667 (s, C=O) cm$^{-1}$; UV/VIS (CHCl$_3$): λ$_{max}$ (ε)=638 (67860), 694 (157030) nm.

Analytical Data on Example 35:
Elemental analysis (% by weight calc./found): C: 56.05/55.9; H: 3.2/3.2; N: 1.7/1.7; O: 7.85/7.9; I: 31.2/31.3; Mass (FD, 8 kV): m/z=1628.4 [M$^+$, 100%]; IR (KBr): ν=1709 (s, C=O), 1667 (s, C=O) cm$^{-1}$; UV/VIS (CHC$_3$): λ$_{max}$ (E) =624 (53220), 667 (129770) nm.

Analytical Data on Example 36:
Elemental analysis (% by weight calc./found): C: 82.4/82.3; H: 7.7/7.7; N: 1.8/1.8; O: 8.1/8.2; Mass (FD, 8 kV): m/z=1573.5 [M$^+$, 100%]; IR (KBr): ν=1709 (s, C=O), 1667 (s, C=O) cm$^{-1}$; UV/VIS (CHCl$_3$): λ$_{max}$ (ε)=624 (54010), 673 (129770) nm.

Analytical Data on Example 37:
Element analysis (% by weight calc./found): C: 76.75/76.6; H: 4.75/4.75; N: 2.35/2.35; O: 5.4/5.45; S: 10.75/10.85; Mass (FD, 8 kV): m/z=1188.9 [M$^+$, 100%]; IR (KBr): ν=1707 (s, C=O), 1668 (s, C=O) cm$^{-1}$; UV/VIS (CHCl$_3$): λ$_{max}$ (ε)=635 (68880), 691 (160210) nm.

Analytical Data on Example 49:
Elemental analysis (% by weight calc./found): C: 66.3/66.2; H: 3.95/3.95; N: 2.05/2.1; O: 9.3/9.35; I: 18.4/18.4; Mass (FD, 8 kV): m/z=1376.3 [M$^+$, 100%]; IR (KBr): ν=1709 (s, C=O), 1667 (s, C=O) cm$^{-1}$; UV/VIS (CHCl$_3$): λ$_{max}$ (ε)=624 (56040), 672 (134830) nm.

Analytical Data on Example 50:
Elemental analysis (% by weight calc./found): C: 79.5/79.3; H: 5.7/5.7; N: 2.2/2.2; O: 7.55 /7.7; S: 5.05/5.1; Mass (FD, 8 kV): m/z=1269.0 [M$^+$, 100%]; IR (KBr): ν=1708 (s, C=O), 1669 (s, C=O) cm$^{-1}$; UV/VIS (CHCl$_3$): λ$_{max}$ (ε)=630 (61650), 686 (143410) nm.

We claim:
1. A 1,6,9,14-tetrasubstituted terrylenetetracarboxylic diimide of the general formula I

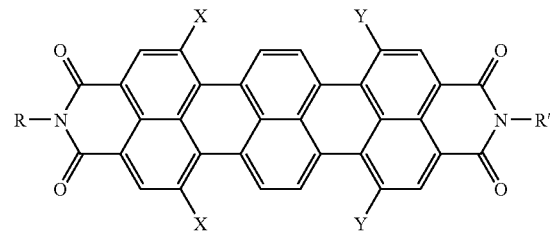

in which the variables are defined as follows:
X and Y are each independently
  bromine; cyano;
  aryloxy, arylthio, hetaryloxy or hetarylthio, each of which may be mono- or polysubstituted by $C_1$-$C_{12}$-alkyl, $C_1$-$C_{12}$-alkoxy, —COOR$^1$, —SO$_3$R$^1$, halogen, hydroxyl, cyano, —CONHR$^2$ and/or —NHCOR$^2$;
  a radical of the formula -L-R$^3$;
  a radical of the formula —NR$^2$$_2$;
R and R' are each independently
  hydrogen;
  $C_1$-$C_{30}$-alkyl whose carbon chain may be interrupted by one or more —O—, —S—, —NR$^1$—, —CO— and/or —SO$_2$— groups, and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical which is bonded via a nitrogen atom and may contain further heteroatoms and be aromatic;

C$_5$-C$_8$-cycloalkyl whose carbon skeleton may be interrupted by one or more —O—, —S— and/or —NR$^1$— groups, and/or which may be mono- or polysubstituted by C$_1$-C$_6$-alkyl;

aryl or hetaryl which may be mono- or polysubstituted by C$_1$-C$_{18}$-alkyl, C$_1$-C$_6$-alkoxy, cyano, —CONHR$^2$, —NHCOR$^2$ and/or aryl or hetarylazo, each of which may be substituted by C$_1$-C$_{10}$-alkyl, C$_1$-C$_6$-alkoxy or cyano;

L is 1,2-ethylene, 1,2-ethenylene or 1,2-ethynylene;

R$^1$ is hydrogen or C$_1$-C$_6$-alkyl;

R$^2$ is hydrogen; C$_1$-C$_{18}$-alkyl; aryl or hetaryl, each of which may be substituted by C$_1$-C$_6$-alkyl, C$_1$-C$_6$-alkoxy, halogen, hydroxyl, carboxyl or cyano;

R$^3$ is C$_1$-C$_{18}$-alkyl whose carbon chain may be interrupted by one or more —O—, —S—, —NR$^1$—, —CO— and/or —SO$_2$— groups, and may be mono- or polysubstituted by —COOR$^1$, —SO$_3$R$^1$, hydroxyl, cyano, C$_1$-C$_6$-alkoxy, aryl which may be substituted by C$_1$-C$_{18}$-alkyl or C$_1$-C$_6$-alkoxy, and/or a 5- to 7-membered heterocyclic radical which is bonded via a nitrogen atom and may contain further heteroatoms and be aromatic.

2. A 1,6,9,14-tetrasubstituted terrylenetetracarboxylic diimide of the formula I as claimed in claim 1, in which the variables are defined as follows:

X and Y are each independently bromine; cyano;

phenoxy, phenylthio, pyridyloxy or pyridylthio, each of which may be mono- or polysubstituted by C$_1$-C$_{12}$-alkyl, C$_1$-C$_{12}$-alkoxy, —COOR$^1$, halogen, hydroxyl, cyano, —CONHR$^2$ and/or —NHCOR$^2$;

a radical of the formula -L-R$^3$;

R and R' are each independently hydrogen;

C$_1$-C$_{30}$-alkyl whose carbon chain may be interrupted by one or more —O— and/or —CO— groups, and which may be mono- or polysubstituted by cyano, C$_1$-C$_6$-alkoxy and/or aryl which may be substituted by C$_1$-C$_{18}$-alkyl or C$_1$-C$_6$-alkoxy;

C$_5$-C$_8$-cycloalkyl which may be mono- or polysubstituted by C$_1$-C$_6$-alkyl;

phenyl, naphthyl or pyridyl which may be mono- or polysubstituted by C$_1$-C$_{18}$-alkyl, C$_1$-C$_6$-alkoxy, cyano, —CONHR$^2$ and/or —NHCOR$^2$;

L is 1,2-ethenylene or 1,2-ethynylene;

R$^1$ is hydrogen or C$_1$-C$_6$-alkyl;

R$^2$ is hydrogen; C$_1$-C$_{18}$-alkyl; phenyl which may be substituted by C$_1$-C$_6$-alkyl, C$_1$-C$_6$-alkoxy, halogen, hydroxyl, carboxyl or cyano;

R$^3$ is C$_1$-C$_{18}$-alkyl whose carbon chain may be interrupted by one or more —O— and/or —CO— groups, and which may be mono- or polysubstituted by —COOR$^1$, hydroxyl, cyano, C$_1$-C$_6$-alkoxy and/or aryl which may be substituted by C$_1$-C$_{18}$-alkyl or C$_1$-C$_6$-alkoxy.

3. A process for preparing 1,6,9,14-tetrasubstituted terrylene-tetracarboxylic diimides of the general formula Ia

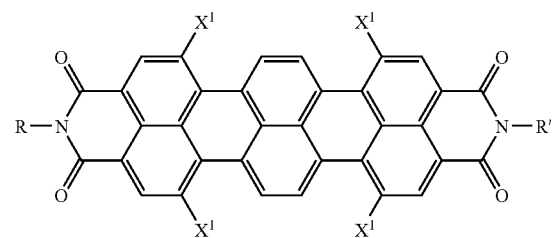

Ia in which the variables are defined as follows:

X$^1$ is bromine; aryloxy, arylthio, hetaryloxy or hetarylthio, each of which may be mono- or polysubstituted by C$_1$-C$_{12}$-alkyl, C$_1$-C$_{12}$-alkoxy, —COOR$^1$, —SO$_3$R$^1$, halogen, hydroxyl, cyano, —CONHR$^2$ and/or —NHCOR$^2$;

R and R' are each independently hydrogen;

C$_1$-C$_{30}$-alkyl whose carbon chain may be interrupted by one or more —O—, —S—, —NR$^1$—, —CO— and/or —SO$_2$— groups, and which may be mono- or polysubstituted by cyano, C$_1$-C$_6$-alkoxy, aryl which may be substituted by C$_1$-C$_{18}$-alkyl or C$_1$-C$_6$-alkoxy, and/or a 5- to 7-membered heterocyclic radical which is bonded via a nitrogen atom and may contain further heteroatoms and be aromatic;

C$_5$-C$_8$-cycloalkyl whose carbon skeleton may be interrupted by one or more —O—, —S— and/or —NR$^1$— groups, and/or which may be mono- or polysubstituted by C$_1$-C$_6$-alkyl;

aryl or hetaryl, each of which may be mono- or polysubstituted by C$_1$-C$_{18}$-alkyl, C$_1$-C$_6$-alkoxy, cyano, —CONHR$^2$, —NHCOR$^2$ and/or aryl or hetarylazo, each of which may be substituted by C$_1$-C$_{10}$-alkyl, C$_1$-C$_6$-alkoxy or cyano;

R$^1$ is hydrogen or C$_1$-C$_6$-alkyl;

R$^2$ is hydrogen; C$_1$-C$_{18}$-alkyl; aryl or hetaryl, each of which may be substituted by C$_1$-C$_6$-alkyl, C$_1$-C$_6$-alkoxy, halogen, hydroxyl, carboxyl or cyano, which comprises a) reacting a terrylenetetracarboxylic diimide of the general formula II

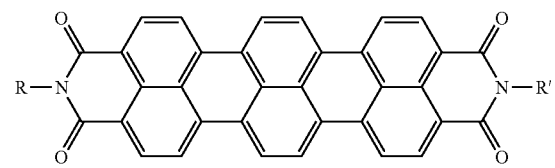

II with elemental bromine in the presence of a halohydrocarbon as solvent to give the 1,6,9,14-tetrabromoterrylenetetracarboxylic diimide of the general formula Ia'

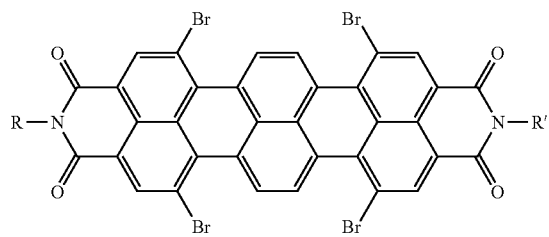

and, if desired, b) converting the tetrabromoterrylenetetracarboxylic diimide Ia' obtained in step a) in the presence of an inert nitrogen-basic solvent and a base with an alcohol or thioalcohol of the general formula III where $X^1 \ne Br$ $$X^1\text{—H} \qquad \qquad III$$

to the 1,6,9,14-tetrasubstituted terrylenetetracarboxylic diimide of the formula Ia where $X^1 \ne$ bromine.

4. A process for preparing 1,6,9,14-tetrasubstituted terrylenetetracarboxylic dimides of the general formula Ib

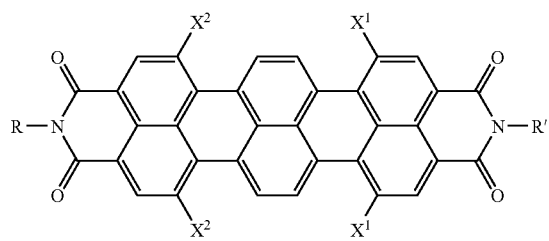

in which the variables are defined as follows:

$X^2$ is aryloxy, arylthio, hetaryloxy or hetarylthio, each of which may be mono- or polysubstituted by $C_1$-$C_{12}$-alkyl, $C_1$-$C_{12}$-alkoxy, —$COOR^1$, —$SO_3R^1$, cyano, —$CONHR^4$ and/or —$NHCOR^4$;

$X^1$ is bromine; aryloxy, arylthio, hetaryloxy or hetarylthio, each of which may be mono- or polysubstituted by $C_1$-$C_{12}$-alkyl, $C_1$-$C_{12}$-alkoxy, —$COOR^1$, —$SO_3R^1$, halogen, hydroxyl, cyano, —$CONHR^2$ and/or —$NHCOR^2$;

R and R' are each independently hydrogen;

$C_1$-$C_{30}$-alkyl whose carbon chain may be interrupted by one or more —O—, —S—, —$NR^1$—, —CO— and/or —$SO_2$— groups, and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical which is bonded via a nitrogen atom and may contain further heteroatoms and be aromatic;

$C_5$-$C_8$-cycloalkyl whose carbon skeleton may be interrupted by one or more —O—, —S— and/or —$NR^1$— groups, and/or which may be mono- or polysubstituted by $C_1$-$C_6$-alkyl;

aryl or hetaryl, each of which may be mono- or polysubstituted by $C_1$-$C_{18}$-alkyl, $C_1$-$C_6$-alkoxy, cyano, —$CONHR^2$, —$NHCOR^2$ and/or aryl or hetarylazo, each of which may be substituted by $C_1$-$C_{10}$-alkyl, $C_1$-$C_6$-alkoxy or cyano;

$R^1$ is hydrogen or $C_1$-$C_6$-alkyl;

$R^2$ is hydrogen; $C_1$-$C_{18}$-alkyl; aryl or hetaryl, each of which may be substituted by $C_1$-$C_6$-alkyl, $C_1$-$C_6$-alkoxy, halogen, hydroxyl, carboxyl or cyano, $R^4$ is $C_1$-$C_{18}$-alkyl; aryl or hetaryl, each of which may be substituted by $C_1$-$C_6$-alkyl, $C_1$-$C_6$-alkoxy, hydroxyl or cyano, which comprises a) reacting a 1,6-disubstituted terrylenetetracarboxylic diimide of the general formula IV

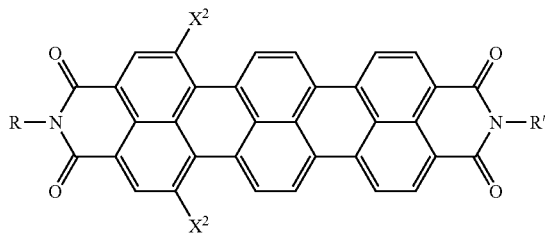

with elemental bromine in the presence of a halohydrocarbon as solvent to give the 9,14-dibrominated terrylenetetracarboxylic diimide of the general formula Ib'

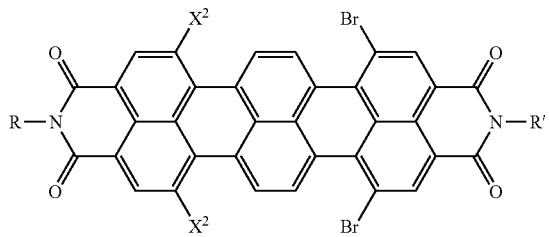

and, if desired, b) converting the 9,14-dibrominated terrylenetetracarboxylic diimide Ib' obtained in step a) in the presence of an inert nitrogen-basic solvent and a base with an alcohol or thioalcohol of the general formula III where $X^1 \ne$ bromine $$X^1\text{—H} \qquad \qquad III$$

to the 1,6,9,14-tetrasubstituted terrylenetetracarboxylic diimide of the formula Ib where $X^1 \ne$ bromine.

5. A process for preparing 1,6,9,14-tetrasubstituted terrylene-tetracarboxylic diimides of the general formula Ic

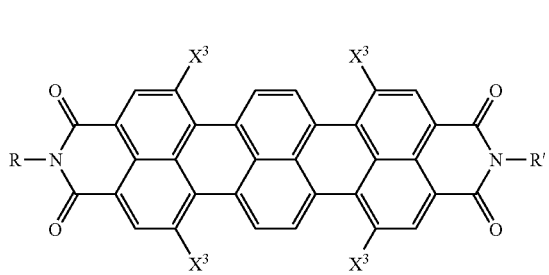

in which the variables are defined as follows:

$X^3$ is a radical of the formula -L-$R^3$;

R and R' are each independently hydrogen;

$C_1$-$C_{30}$-alkyl whose carbon chain may be interrupted by one or more —O—, —S—, —$NR^1$—, —CO— and/ or —SO$_2$— groups, and which may be mono- or polysubstituted by cyano, C$_1$-C$_6$-alkoxy, aryl which may be substituted by C$_1$-C$_{18}$-alkyl or C$_1$-C$_6$-alkoxy, and/or a 5- to 7-membered heterocyclic radical which is bonded via a nitrogen atom and may contain further heteroatoms and be aromatic;

C$_5$-C$_8$-cycloalkyl whose carbon skeleton may be interrupted by one or more —O—, —S— and/or —NR$^1$— groups, and/or which may be mono- or polysubstituted by C$_1$-C$_6$-alkyl;

aryl or hetaryl, each of which may be mono- or polysubstituted by C$_1$-C$_{18}$-alkyl, C$_1$-C$_6$-alkoxy, cyano, —CONHR$^2$, —NHCOR$^2$ and/or aryl or hetarylazo, each of which may be substituted by C$_1$-C$_{10}$-alkyl, C$_1$-C$_6$-alkoxy or cyano;

L is 1,2-ethylene, 1,2-ethenylene or 1,2-ethynylene;

R$^1$ is hydrogen or C$_1$-C$_6$-alkyl;

R$^2$ is hydrogen; C$_1$-C$_{18}$-alkyl; aryl or hetaryl, each of which may be substituted by C$_1$-C$_6$-alkyl, C$_1$-C$_6$-alkoxy, halogen, hydroxyl, carboxyl or cyano;

R$^3$ is C$_1$-C$_{18}$-alkyl whose carbon chain may be interrupted by one or more —O—, —S—, —NR$^1$—, —CO— and/or —SO$_2$— groups, and may be mono- or polysubstituted by —COOR$^1$, —SO$_3$R$^1$, hydroxyl, cyano, C$_1$-C$_6$-alkoxy, aryl which may be substituted by C$_1$-C$_{18}$-alkyl or C$_1$-C$_6$-alkoxy, and/or a 5- to 7-membered heterocyclic radical which is bonded via a nitrogen atom and may contain further heteroatoms and be aromatic, which comprises reacting a 1,6,9,14-tetrabromoterrylenetetracarboxylic diimide of the general formula Ia'

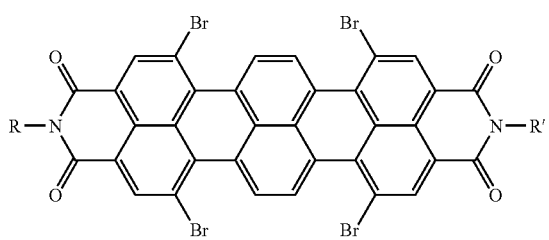

Ia' in the presence of an aprotic solvent, a palladium complex as a catalyst, a copper salt as a cocatalyst and a base with a 1-alkyne of the general formula V

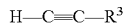  V and, if desired, additionally reducing the unsaturated bonds present in the X$^3$ radicals of the 1,6,9,14-tetrasubstituted terrylenetetracarboxylic diimide obtained.

6. A process for preparing 1,6,9,14-tetrasubstituted terrylenetetracarboxylic diimides of the general formula Id

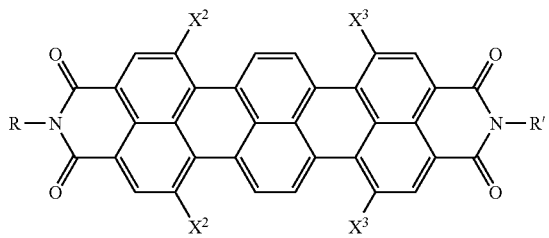

Id in which the variables are defined as follows:

X$^2$ is aryloxy, arylthio, hetaryloxy or hetarylthio, each of which may be mono- or polysubstituted by C$_1$-C$_{12}$-alkyl, C$_1$-C$_{12}$-alkoxy, —COOR$^1$, —SO$_3$R$^1$, cyano, —CONHR$^4$ and/or —NHCOR$^4$;

X$^3$ is a radical of the formula -L-R$^3$;

R and R' are identical or different and are each independently hydrogen;

C$_1$-C$_{30}$-alkyl whose carbon chain may be interrupted by one or more —O—, —S—, —NR$^1$—, —CO— and/or —SO$_2$— groups, and which may be mono- or polysubstituted by cyano, C$_1$-C$_6$-alkoxy, aryl which may be substituted by C$_1$-C$_{18}$-alkyl or C$_1$-C$_6$-alkoxy, and/or a 5- to 7-membered heterocyclic radical which is bonded via a nitrogen atom and may contain further heteroatoms and be aromatic;

C$_5$-C$_8$-cycloalkyl whose carbon skeleton may be interrupted by one or more —O—, —S— and/or —NR$^1$— groups, and/or which may be mono- or polysubstituted by C$_1$-C$_6$-alkyl;

aryl or hetaryl, each of which may be mono- or polysubstituted by C$_1$-C$_{18}$-alkyl, C$_1$-C$_6$-alkoxy, cyano, —CONHR$^2$, —NHCOR$^2$ and/or aryl or hetarylazo, each of which may be substituted by C$_1$-C$_{10}$-alkyl, C$_1$-C$_6$-alkoxy or cyano;

is 1,2-ethylene, 1,2-ethenylene or 1,2-ethynylene;

R$^1$ is hydrogen or C$_1$-C$_6$-alkyl;

R$^2$ is hydrogen; C$_1$-C$_{18}$-alkyl; aryl or hetaryl, each of which may be substituted by C$_1$-C$_6$-alkyl, C$_1$-C$_6$-alkoxy, halogen, hydroxyl, carboxyl or cyano;

R$^3$ is C$_1$-C$_{18}$-alkyl whose carbon chain may be interrupted by one or more —O—, —S—, —NR$^{1'}$, —CO— and/or —SO$_2$— groups, and may be mono- or polysubstituted by —COOR$^1$, —SO$_3$R$^1$, hydroxyl, cyano, C$_1$-C$_6$-alkoxy, aryl which may be substituted by C$_1$-C$_{18}$-alkyl or C$_1$-C$_6$-alkoxy, and/or a 5- to 7-membered heterocyclic radical which is bonded via a nitrogen atom and may contain further heteroatoms and be aromatic;

R$^4$ is C$_1$-C$_{18}$-alkyl; aryl or hetaryl, each of which may be substituted by C$_1$-C$_6$-alkyl, C$_1$-C$_6$-alkoxy, halogen, hydroxyl, carboxyl or cyano, which comprises reacting a 9,14-dibrominated terrylenetetracarboxylic diimide of the general formula Ib'

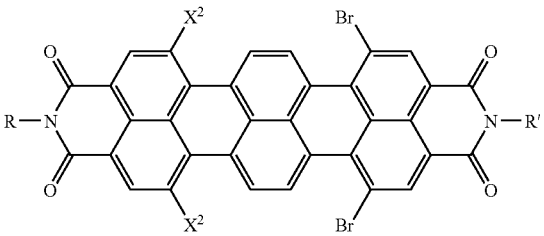

Ib' in the presence of an aprotic solvent, a palladium complex as a catalyst, a copper salt as a cocatalyst and a base with a 1-alkyne of the general formula V

  V and, if desired, additionally reducing the unsaturated bonds present in the X$^3$ radicals of the 1,6,9,14-tetrasubstituted terrylenetetracarboxylic diimide obtained.

7. A colored high molecular weight organic material and a colored inorganic material comprising the 1,6,9,14-tetrasubstituted terrylenetetracarboxylic diimide of formula I as claimed in claim 1.

8. A method for coloring a high molecular weight organic material and an inorganic material comprising adding the 1,6,9,14-tetrasubstituted terrylenetetracarboxylic diimide of formula I as claimed in claim 1 to the high molecular weight organic material and the inorganic material.

9. A dispersing aid, a pigment additive for organic pigments, an intermediate for preparing fluorescent colorants and a pigment additive comprising the 1,6,9,14-tetrasubstituted terrylenetetracarboxylic diimide of formula I as claimed in claim 1.

10. A method for preparing a dispersing aid, a pigment additive for organic pigments, an intermediate for preparing fluorescent colorants and a pigment additive comprising adding the 1,6,9,14-tetrasubstituted terrylenetetracarboxylic diimide of formula I as claimed in claim 1 to a dispersing aid, a pigment additive for organic pigments, an intermediate for preparing fluorescent colorants and a pigment additive.

11. An aqueous polymer dispersion which is colored or absorbs and/or emits in the near infrared region of the electromagnetic spectrum comprising the 1,6,9,14-tetrasubstituted terrylenetetracarboxylic diimide of formula I as claimed in claim 1.

12. A method for preparing an aqueous polymer dispersion which is colored or absorbs and/or emits in the near infrared region of the electromagnetic spectrum comprising adding the 1,6,9,14-tetrasubstituted terrylenetetracarboxylic diimide of formula I as claimed in claim 1 to the aqueous polymer dispersion.

13. An emitter in electroluminescence and chemiluminescence applications, an active component in fluorescence conversion, a bioluminescence array, a photovoltaic and a laser dye comprising the 1,6,19,14-tetrasubstituted terrylenetetracarboxylic diimide of formula I as claimed in claim 1.

* * * * *